(12) United States Patent
Freeze et al.

(10) Patent No.: US 10,588,979 B1
(45) Date of Patent: Mar. 17, 2020

(54) CANNABINOID AND TERPENE-INFUSED TOPICAL CREAM

(71) Applicants: Cody D. Freeze, Pratt, KS (US);
 Allison N. Freeze, Pratt, KS (US)

(72) Inventors: Cody D. Freeze, Pratt, KS (US);
 Allison N. Freeze, Pratt, KS (US)

( * ) Notice: Subject to any disclaimer, the term of this patent is extended or adjusted under 35 U.S.C. 154(b) by 0 days.

(21) Appl. No.: 16/133,572

(22) Filed: Sep. 17, 2018

(51) Int. Cl.
| | |
|---|---|
| *A61K 31/047* | (2006.01) |
| *A61K 47/46* | (2006.01) |
| *A61K 9/00* | (2006.01) |
| *A61K 9/06* | (2006.01) |
| *A61K 47/22* | (2006.01) |
| *A61K 47/10* | (2017.01) |
| *A61K 45/06* | (2006.01) |
| *A61K 47/24* | (2006.01) |
| *A61K 31/352* | (2006.01) |
| *A61K 31/045* | (2006.01) |
| *A61K 31/11* | (2006.01) |
| *A61K 31/122* | (2006.01) |
| *A61K 31/35* | (2006.01) |
| *A61K 47/18* | (2017.01) |

(52) U.S. Cl.
CPC ............ *A61K 47/46* (2013.01); *A61K 9/0014* (2013.01); *A61K 9/06* (2013.01); *A61K 31/045* (2013.01); *A61K 31/047* (2013.01); *A61K 31/11* (2013.01); *A61K 31/122* (2013.01); *A61K 31/35* (2013.01); *A61K 31/352* (2013.01); *A61K 45/06* (2013.01); *A61K 47/10* (2013.01); *A61K 47/18* (2013.01); *A61K 47/22* (2013.01); *A61K 47/24* (2013.01)

(58) Field of Classification Search
CPC ..................................................... A61K 31/047
See application file for complete search history.

(56) References Cited

U.S. PATENT DOCUMENTS

| | | | | |
|---|---|---|---|---|
| 2010/0273895 | A1* | 10/2010 | Stinchcomb | A61K 9/0014 514/733 |
| 2010/0324111 | A1* | 12/2010 | Voegel | A61K 9/0014 514/423 |
| 2012/0258059 | A1* | 10/2012 | Iwama | A61K 8/64 424/59 |
| 2016/0256411 | A1* | 9/2016 | Aung-Din | A61K 9/0017 |

* cited by examiner

*Primary Examiner* — Benjamin J Packard
(74) *Attorney, Agent, or Firm* — Kevin Fortin

(57) ABSTRACT

The present invention discloses a topical composition comprising terpene blend and cannabidiol (CBD) or a derivative thereof, useful for managing pain, the treatment or prevention of inflammatory skin disorders, and treatment methods thereof. The composition includes 2-pyrrolidone-5-carboxylic acid and a blend of antioxidants to optimize tissue health.

17 Claims, No Drawings

CANNABINOID AND TERPENE-INFUSED TOPICAL CREAM

FIELD OF THE INVENTION

The present invention is generally directed to novel compositions and methods for treatment of dermatologic conditions. More particularly, a composition comprising Terpene and cannabidiol (CBD) or derivatives thereof for treating inflammatory skin disorders. Further, the composition relates to cosmetic compositions for the protection and treatment of the skin.

BACKGROUND OF THE INVENTION

It is known that skin diseases in human are very common. There are several factors such as atmospheric conditions in winter, repeated contact with detergent when washing crockery and carrying out domestic chores, the sun's rays, contact with various chemicals can result in dryness of the skin, blotchiness and even in more severe damage. Further, there are many inflammatory skin diseases caused due to genetic disorder and pathogens.

Inflammatory skin diseases are a group of diseases that results in inflammation of the skin. These diseases are characterized by itchiness, red skin, and a rash. Psoriasis, also known as psoriasis vulgaris, is a chronic, inflammatory skin disease characterized by red, scaly patches, papules, and plaques, which usually itch. Psoriasis is also associated with an increased risk of certain cancers, cardiovascular disease, and other immune-mediated disorders such as Crohn's disease and ulcerative colitis. Psoriasis characterized by accelerated growth of epidermis cells (keratinocyte cells) accompanied by an inflammation. No cure is available for psoriasis, but various topical and systemic treatments can help control the symptoms.

Various types of compositions of cannabinoid are known in the prior art for use in therapeutic treatment of disease, disorder or various medical conditions. Cannabinoid have also shown to inhibit keratinocyte proliferation which is induced in psoriasis. They also have shown anti-inflammatory properties that may be beneficial for treatment of psoriasis.

Cannabis or Cannabinoid is used as a drug and as medicine. The constituent of cannabis is tetrahydrocannabinol (THC), including many other cannabinoids, such as cannabidiol (CBD), cannabinol (CBN), tetrahydrocannabivarin (THCV) and cannabigerol (CBG).

Further, terpenes have important roles in cannabinoid-comprising products, affecting the functionality and bioavailability of the cannabinoids and the aroma of the product.

Processing cannabis plant material typically leads to terpenes loss so that most of cannabis products are of relatively low terpene content.

Terpenes and terpenoids are natural volatile non-aromatic compounds found as components of essential oils present in many plants and contain a carbon and hydrogen (terpenes) or a carbon, hydrogen, and oxygen scaffold (terpenoids). Terpenes and terpenoids have been used as skin penetration agents, as well as fragrances and flavouring agents.

Therefore, there is a need for terpene blend composition for topical use with minimal adverse effects that is specifically useful for treatment of inflammatory skin disorders and conditions.

SUMMARY OF THE INVENTION

Provided herein are formulations and compositions for a topical pain cream to be used as needed for treatment of inflammatory skin disorders and conditions. In one embodiment, the composition is used directly on or under the skin. In one embodiment, the composition is used but not limited to itching, swelling or painful joints. In one embodiment, the composition may also be used on any areas of dryness or scaling, as certain components may enhance moisture retention. In one embodiment, the composition may work well on sunburns and burns of thermal (non-chemical). In one embodiment, the composition is non-toxic in nature and used in cosmetics medical, pharmaceutical and nutraceutical applications.

The composition of the Terpenes and cannabinoids derivatives have very effective roles in anti-inflammatory skin diseases. Preferably, the composition contain a humectant. In one embodiment, the humectant includes esters of terpene alcohols with 2-pyrrolidone-5-carboxylic acid, which are physiologically active substances capable of passing through the stratum corneum into the living layers of the epidermis and provides an anti-inflammatory effect. The humectant to stabilizes the cream to open air and to allow cream applied to the skin of a subject to be protected from evaporation.

In one embodiment, the humectant is selected from the group consisting of 2-pyrrolidone-5-carboxylic acid, sodium pidolate, propylene glycol, urea, and combinations thereof.

In one embodiment, the composition include 2-pyrrolidone-5-carboxylic acid as the sole humectant, which has been shown to release GABA from the cerebral cortex and displays anti-anxiety effects in some studies. 2-pyrrolidone-5-carboxylic acid is understood to relax a localized region of the body when applied topically, and to reduce inflammation when combined with plant terpenes.

In one aspect of the present invention provide Terpene-Infused Topical Cream, which composition is prepared by mixing of Versapro cream base, terpene blend, glycerin, sunflower liquid lecithin, propylene glycol, and cannabidiol (CBD) bulk isolate powder sourced from industrial hemp or other cannabinoids such as cannabinol (CBN), tetrahydrocannabinol (THC), tetrahydrocannabivarin (THCV) and cannabigerol (CBG).

Further, in one aspect of the present invention a terpene infused topical cream composition 250 mg CBD/30 mL comprising by weight of 8 mL or 6.513 grams of terpene blend, 2 mL or 2.594 grams of glycerin, 2 mL or 2.094 grams of sunflower liquid lecithin, 2 mL or 2.091 grams of propylene glycol, 1.575 grams of cannabidiol (CBD), and 165.208 grams of Versapro cream base.

In another aspect of the invention, the topical cream composition includes a cream base including aloe extract, 1-10% on a weight to weight basis of the composition is a terpene blend selected from the group consisting of: geraniol, citronellol, geranial, citronellal, linalool, menthone, rose oxide, alpha-terpineol, a pharmaceutically acceptable salt, ester or solvate thereof, or any combination thereof, 1-10% on a weight to weight basis of the composition is glycerin, 1-10% on a weight to weight basis of the composition is sunflower liquid lecithin, 1-10% on a weight to weight basis of the composition is propylene glycol, 0.1-10% on a weight to weight basis of the composition of 2-pyrrolidone-5-carboxylic acid, and 1-10% on a weight to weight basis of the composition is cannabidiol (CBD).

Further, in one aspect of the present invention, the cannabidiol (CBD) is greater than 95% purity (which means 5% loss or >/=95% purity CBD isolate powder).

Further, in one aspect of the present invention the Terpene infused topical cream composition 250 mg CBD/30 mL, a Terpene blend is prepared which is mainly used for targeting pain/inflammation. This blend is similar to found naturally in the cannabis strain/chemovar "White Widow". It provides multiple specifically chosen/formulated terpenes in a blend. This terpene blend is paramount to the success of the entire blend via "Entourage Effects" with the CBD or other cannabinoids (THC, THCV, CBDV, etc.).

The Versapro cream base is a white, smooth and shiny versatile cream with increased pH stability. Versapro cream base is highly moisturizing and odorless act as an emulsifier for oil-in-water. It can be appreciated that analogues to Versapro cream can be substituted in accordance with the present invention.

In another aspect of the present invention provides a method of preparing Terpene-Infused Topical Cream 250 mg CBD/30 mL composition for topical use, the composition is prepared by mixing to an ointment jar or similar apparatus, the ingredients are: 8 mL or 6.513 grams of terpene blend, 1.575 grams of cannabidiol (CBD), 2 mL or 2.094 grams of sunflower liquid lecithin, 2 mL or 2.594 grams of glycerin, and 2 mL or 2.091 grams of propylene glycol. Then, the ointment jar is placed into an Unguator® machine. It is noted that a torsion balance is used to weigh each ingredient individually. It has a specificity of at least the hundred-thousandths of a gram.

In another aspect of the present invention, the ointment jar is of capacity of 200 mL without limiting the scope of the invention. The jar may be used different size and therefore the ingredients can vary accordingly. The jar is placed on the Unguator® machine, and by selecting "Standard-Pregrind", the spin blade blends the ingredient homogeneously in 5 and 15 minutes. Once spin is complete with standard pregrind, 165.208 grams of Versapro cream base is added. Further a screw-on top of 200 mL ointment jar is added and placed on stage for Unguator use for emulsion for 3 to 10 minutes for the Unguator® machine to blend. As a result, the Terpene-Infused Topical Cream 250 mg CBD/30 mL is prepared.

Yet another aspect of the present invention, the Terpene-Infused Topical Cream 250 mg CBD/30 mL may be modified to contain various concentrations of cannabinoids and terpenoids, depending on the form and function of intent. Aloe-Vera and other ingredients may also be added, as well as other terpene/cannabinoids. Alternatively, in another aspect, the Terpene-Infused Topical Cream is prepared by using Versapro GEL or PHYTOBASE, rather than Versapro.

An exemplary embodiment of the invention includes a Terpene infused topical cream composition. This composition includes 100-300 grams of Versapro cream base, 1-20 grams of an isolated terpene, or a blend of isolated terpenes selected from the group consisting of: geraniol, citronellol, geranial, citronellal, linalool, menthone, rose oxide, alpha-terpineol, a pharmaceutically acceptable salt, ester or solvate thereof, or any combination thereof, 1-10 grams of glycerin, 1-10 grams of sunflower liquid lecithin, 1-10 grams of propylene glycol, and less than ten grams of 2-pyrrolidone-5-carboxylic acid. This composition includes 1-10 grams of cannabidiol (CBD), or other bioactive cannabinoid, or combination of cannabinoids such as those disclosed herein or any other cannabinoid. Cannabinoids are defined as any bioactive substance that has detectable effect on the CB1 or CB2 receptors in the human endocannabinoid system.

The isolated terpenes, the isolated CBD, or other isolated cannabinoids, can be derived from *Cannabis sativa* l, other suitable plant, synthesized, or derived from yeast or other engineered microbe source. The cannabinoids or terpenes, or both, can also be derived from a whole plant extract of *Cannabis sativa* l in various embodiments of the invention.

It will be understood that certain ingredients can be added to the compositions described herein without materially affecting the basic and novel properties of the compositions described herein. For example, the compositions can include undisclosed and/or unclaimed ingredients that do not materially affect the basic and novel properties of the compositions described herein, therapeutic or otherwise. Examples of such ingredients include fragrance and moisturiser that provide a more pleasant appearance and/or odor, but do not materially affecting the desired properties, therapeutic or otherwise, of the compositions described herein.

Other variations, embodiments and features of the present disclosure will become evident from the following detailed description, abstract and claims.

DETAILED DESCRIPTION

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

The term "formulation" includes the compositions described herein and any additional components that are desired for use of the composition to a user or for topical use of the composition by a user.

The term "treating" or "treatments" or "prevention" as used herein can include any of the following: alleviating, reducing, improving, mitigating, or eliminating a disease, disorder or medical condition.

The term "cannabinoid" as used herein can include any form of cannabis or cannabis derivatives. The cannabis comprises tetrahydrocannabinol (THC), and/or other cannabinoids, such as cannabidiol (CBD), cannabinol (CBN), tetrahydrocannabivarin (THCV) and cannabigerol (CBG). In one embodiment, the cannabis comprises natural, neutral, or acidic forms of the cannabinoids, or semi-synthetic and synthetic derivatives thereof. In one embodiment, the cannabis comprises terpenes and/or flavonoids.

As used herein, the term "terpene" or "terpene blend" is intended to refer to one or more of: a terpene, a terpenoid, or a pharmaceutically acceptable is salt, ester or solvate thereof. A "terpenoid" is a chemically modified terpene. Examples of terpenoids include, but are not limited to, terpenoid aldehydes, terpenoid acids, terpenoid esters and terpenoid oxides.

In accordance with a specific embodiment of the present invention, the terpene compound in the composition is geraniol, citronellol, geranial, citronellal, linalool, menthone, rose oxide, alpha-terpineol, a pharmaceutically acceptable is salt, ester or solvate thereof, or any mixture thereof.

In one embodiment of the invention, the compositions described herein comprise, consist, consist essentially of, include, include essentially of the recited ingredients.

The composition described herein are useful for the treatment and prevention of a wide range of diseases, disorders or medical conditions, including, for example, inflammation, inflammatory skin diseases, itching, swelling or painful joints, dryness or scaling, sunburns and burns of thermal (non-chemical). The present composition has sufficient transdermal capability to reduce local pain of the skin, musculature, connective tissue, joints and neuropathic pain. Further, the composition is non-toxic in nature and used in cosmetics medical, pharmaceutical and nutraceutical applications.

An example of an embodiment is a composition of Terpene-Infused Topical Cream comprising (i) Versapro cream base (165.208 grams), (ii) terpene blend (8 mL or 6.513 grams), (iii) glycerin (2 mL or 2.594 grams), (iv) sunflower liquid lecithin (2 mL or 2.094 grams), (iv) propylene glycol (2 mL or 2.091 grams), and (v) cannabidiol (CBD) bulk isolate powder sourced from industrial hemp (1.575 grams for CBD isolate). It can be appreciated that alternate embodiments can vary each of the above mentioned ingredients by up to 20%.

The composition of the present invention includes at least one antioxidant, in addition to CBD. In one embodiment, the Versapro cream base is a white, smooth and shiny versatile cream with an increased pH stability. Further, the Versapro cream base is highly moisturizing and odorless, also facilitates emulsification of the present invention.

Preferably, the Versapro cream base has two primary bio-active ingredients: Aloe and vitamin E. Aloe is defined as any whole plant extract of the plant of the genus *aloe*, or synthetic analogues thereto. In one embodiment, isolated compounds of the *aloe* plant are combined to form the aloe. Aloe has a cooling, soothing and anti-inflammatory effect on the skin when applied topically to accelerate healing of many skin conditions. The use of Versapro cream, which is understood to be safe by the medical community, enables the aloe to be readily and effectively combined with the other ingredients of the present composition. Components of aloe have significant anti-oxidant capability when used topically. The combination of CBD and antioxidants included in aloe extract are complimentary to reduce skin damage and to encourage rapid regeneration of the skin.

The vitamin E is a powerful antioxidant, nutrient and protectant for the skin. When combined with the cannabinoids of the present invention, and the aloe, it complements the anti-inflammatory aspects of the other ingredients with the benefits of a strong antioxidant. The term vitamin E includes the various forms, variants and isoforms of vitamin E, including tocopheryl acetate. The combination of CBD and antioxidants such as vitamin E found in Versapro cream are complimentary to reduce skin damage and to encourage rapid regeneration of the skin.

In one embodiment, the CBD is intended for pain management. It can be the sole pain management ingredient, or be combined with a second pain management ingredient, selected from the group consisting of Ketamine 5-10%, Lidocaine 1-10%, Gabapentin 5-10%; Amitriptyline 2-10%, Imipramine 2-10%, Cyclobenzaprine 2%, Baclofen 2%, Clonidine 0.2%, Ketoprofen 10%, Diclofenac 2-10%, Nifedipine 2-16%, and combinations thereof. The percentages of these second pain management ingredients reflect a concentration of the composition on a weight to weight w:w basis.

In one embodiment, the composition comprising terpene and cannabinoids resulting in a terpene-enriched cannabinoid composition with enhanced therapeutic effect. Whereas the cannabidiol (CBD) is greater than 95% purity (which means 5% loss or >/=95% purity CBD isolate powder).

In one embodiment, the composition is prepared by Terpene blend which is mainly used for targeting pain/inflammation. The blend is similar to the terpene blend found naturally in the cannabis strain/chemovar "White Widow". Terpenes function as anti-inflammatory agents mainly, but as a whole they serve multiple functions in the mix. This terpene blend is paramount to the success of the entire blend via "Entourage Effects" with the cannabidiol (CBD) or other cannabinoids (THC, THCV, CBDV, etc.).

In preferred embodiments, the composition is for a topical use for treatment of inflammatory skin disorders and conditions. In one embodiment, the composition may be used directly on or under the skin.

In alternate embodiment, the composition may be altered to incorporate other various terpenoids and cannabinoids on an as-needed or patient-specific basis.

In another embodiment, a method of preparing Terpene-Infused Topical Cream 250 mg CBD/30 mL composition for topical use is provided. The composition is prepared by mixing the following ingredients to an ointment jar or similar apparatus: 8 mL or 6.513 grams of terpene blend, 1.575 grams of cannabidiol (CBD), 2 mL or 2.094 grams of sunflower liquid lecithin, 2 mL or 2.594 grams of glycerin, and 2 mL or 2.091 grams of propylene glycol. Then, the ointment jar is placed into a Unguator® machine. It is noted that a torsion balance is used to weigh each ingredient individually. It has a specificity of at least the hundred-thousandths of a gram.

In one embodiment, the jar is 200 mL ointment jar without limiting the scope of the invention. The jar may be used different size and therefore the ingredients can vary accordingly.

The jar is placed on the Unguator® machine, and by selecting "Standard-Pregrind", the spin blade blends the ingredient homogeneously in 5 and 15 minutes. Once spin is complete with standard-pregrind, 165.208 grams of Versapro cream base is added. Further a screw-on top of 200 mL ointment jar is added and placed on stage for Unguator use for emulsion for 3 to 10 minutes for the Unguator® machine to blend. As a result, the Terpene-Infused Topical Cream 250 mg CBD/30 mL is prepared.

Thereafter transfer to 30 mL cream/ointment jars. This should make roughly 6 jars at 250 mg CBD/30 mL each given this batch size and recipe.

The Unguator® machine is used for preparation of formulation ointments, cosmetics. The Unguator® machine includes Blade to mix an ointment homogeneously with a slow stroke. It includes an integrated microprocessor measures the actual revolutions of the Mixing Blade. This guarantees that the selected mixing program will always be identical, even for paste-like formulation.

In another embodiment, the Terpene-Infused Topical Cream 250 mg CBD/30 mL may be modified to contain various concentrations of cannabinoids and terpenoids, depending on the form and function of intent. Aloe-Vera and other ingredients may also be added, as well as other terpene/cannabinoids. Alternatively, in another aspect, the Terpene-Infused Topical Cream is prepared by using Versapro GEL or PHYTOBASE, rather than Versapro. The base, while oil-in-water is desired, may be pliable to match application intent.

The Terpene-Infused Topical Cream 250 mg CBD/30 mL is used for treatment and prevention of a wide range of diseases, disorders or medical conditions, including, for example, inflammation, inflammatory skin diseases, itching, swelling or painful joints, dryness or scaling, sunburns and burns of thermal (non-chemical). In one embodiment, 0.5 grams to 4 grams of the Terpene-Infused Topical Cream 250 mg CBD/30 mL is generally recommend using topically to each affected area/joint as needed up to 3 times daily. In one embodiment, the Terpene-Infused Topical Cream 250 mg CBD/30 mL is not intended for oral consumption or use on internal areas/mucous membranes. Further, it is not recommended to be used in the ears, eyes, mouth or any mucous membrane.

Also, it appears that the antioxidant/anti-inflammatory properties of the cream helps with appearances of stretch marks and scarring. It may also have potential as a scar-appearance reducing cream, but all this data is from patient-case reports.

The embodiments described above demonstrate an improved efficacy that is unexpected compared to utilizing the same dose of the same active terpene-cannabinoid product.

In various embodiments, the composition comprises a pharmaceutical product; the dosage forms described herein provide clear separation from the confusion associated with traditional preparations of natural terpene infused products.

Any alterations and further modifications of the compositions and/or formulations described herein, which would normally occur to one skilled in the relevant art and having possession of this disclosure, are to be considered within the scope of the instant claims.

While particular elements, embodiments and applications of the present invention have been shown and described, it will be understood, of course, that the invention is not limited thereto since modifications can be made by those skilled in the art without departing from the scope of the present disclosure, particularly in light of the foregoing teachings.

The invention claimed is:

1. A Terpene-infused topical cream composition having an improved anti-oxidant capacity, comprising:
   a terpene selected from the group consisting of, geraniol, citronellol, geranial, citronellal, linalool, menthone, rose oxide, alpha-terpineol, a pharmaceutically acceptable salt, ester or solvate thereof, or any mixture thereof;
   a humectant;
   cannabidiol (CBD) in a concentration of between 5-10% of the topical cream composition; and
   a carrier including aloe extract and vitamin E, which cooperates with the cannabidiol to function as a topical anti-oxidant.

2. The composition of claim 1, wherein carrier is Versapro cream base to improve emulsification of the topical cream composition.

3. The composition of claim 1, wherein the cannabidiol (CBD) or said derivative of cannabidiol (CBD) has a purity of greater than 95%.

4. The composition of claim 1, wherein the humectant is selected from the group consisting of, 2-pyrrolidone-5-carboxylic acid, sodium pidolate, propylene glycol, urea, and combinations thereof.

5. The composition of claim 4, wherein the humectant is 2-pyrrolidone-5-carboxylic acid.

6. The composition of claim 1, wherein the humectant is sodium pidolate.

7. A terpene infused topical cream composition, comprising:
   a cream base including aloe extract;
   1-10% on a weight to weight basis of the composition is a terpene blend selected from the group consisting of: geraniol, citronellol, geranial, citronellal, linalool, menthone, rose oxide, alpha-terpineol, a pharmaceutically acceptable salt, ester or solvate thereof, or any combination thereof;
   1-10% on a weight to weight basis of the composition is glycerin;
   1-10% on a weight to weight basis of the composition is sunflower liquid lecithin;
   1-10% on a weight to weight basis of the composition is propylene glycol;
   0.1-10% on a weight to weight basis of the composition is 2-pyrrolidone-5-carboxylic acid; and
   1-10% on a weight to weight basis of the composition is cannabidiol (CBD).

8. The composition of claim 7, wherein the terpene blend is selected from a terpene, a terpenoid or terpene derivatives such as but not limited to terpenoid aldehydes, terpenoid acids, terpenoid esters and terpenoid oxides.

9. The composition of claim 7 further comprising a cannabinoid selected from the group consisting of: tetrahydrocannabinol, cannabinol (CBN), tetrahydrocannabivarin (THCV), cannabigerol (CBG), and combinations thereof.

10. A terpene-infused topical cream composition having an improved anti-oxidant capacity, comprising:
    an isolated terpene selected from the group consisting of, geraniol, citronellol, geranial, citronellal, linalool, menthone, rose oxide, alpha-terpineol, a pharmaceutically acceptable salt, ester or solvate thereof, or any mixture thereof;
    a humectant,
    a first pain management ingredient, the first pain management ingredient is isolated cannabidiol (CBD) in a concentration of between 5-10% of the topical cream composition; and
    a carrier including aloe extract and vitamin E, which cooperates with the cannabidiol to function as a topical anti-oxidant.

11. The composition of claim 10, wherein carrier is Versapro cream base to improve emulsification of the topical cream composition.

12. The composition of claim 10, wherein the cannabidiol (CBD) or said derivative of cannabidiol (CBD) has a purity of greater than 95%.

13. The composition of claim 10 further comprising: a second pain management ingredient,
    the second pain management ingredient being selected from the group consisting of Ketamine 5-10%, Lidocaine 1-10%, Gabapentin 5-10%; Amitriptyline 2-10%, Imipramine 2-10%, Cyclobenzaprine 2%, Baclofen 2%, Clonidine 0.2%, Ketoprofen 10%, Diclofenac 2-10%, Nifedipine 2-16%, and combinations thereof, and
    wherein the percentages of the second pain management ingredient reflect a concentration in the composition on a weight to weight w:w basis.

14. The composition of claim 10, wherein the cannabidiol (CBD) has a purity of greater than 95%.

15. The composition of claim 10, wherein the humectant is selected from the group consisting of, 2-pyrrolidone-5-carboxylic acid, sodium pidolate, propylene glycol, urea, and combinations thereof.

16. The composition of claim 10, wherein the humectant is 2-pyrrolidone-5-carboxylic acid.

17. The composition of claim 10, wherein the humectant is sodium pidolate.

* * * * *